(12) United States Patent
Herr et al.

(10) Patent No.: US 6,962,988 B2
(45) Date of Patent: Nov. 8, 2005

(54) EGG SPECIFIC SURFACE PROTEINS

(75) Inventors: John C. Herr, Charlottesville, VA (US); Scott A. Coonrod, Gordonsville, VA (US); Paul Wright, Staunton, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 279 days.

(21) Appl. No.: 10/181,612

(22) PCT Filed: Jan. 19, 2001

(86) PCT No.: PCT/US01/01718
§ 371 (c)(1),
(2), (4) Date: Jul. 18, 2002

(87) PCT Pub. No.: WO01/53339
PCT Pub. Date: Jul. 26, 2001

(65) Prior Publication Data
US 2003/0186369 A1 Oct. 2, 2003

Related U.S. Application Data
(60) Provisional application No. 60/177,123, filed on Jan. 20, 2000.

(51) Int. Cl.[7] .............................................. C07H 21/04
(52) U.S. Cl. .................... 536/23.5; 536/23.1; 435/325; 435/252.3; 530/350; 530/853
(58) Field of Search .............................. 530/350, 853; 536/23.1, 23.5; 435/7.1, 320.1, 325, 252.3; 424/185.1, 94

(56) References Cited

U.S. PATENT DOCUMENTS

| | | | |
|---|---|---|---|
| 4,996,297 A | 2/1991 | Dunbar | |
| 5,602,005 A | 2/1997 | Herr et al. | |
| 5,641,487 A | 6/1997 | Dean | |
| 5,820,863 A | 10/1998 | Dunbar | |
| 5,830,472 A | 11/1998 | Herr et al. | |

FOREIGN PATENT DOCUMENTS

WO    WO 99/65520    12/1999

OTHER PUBLICATIONS

Chavanas et al., "Comparative analysis of the mouse and human peptidylarginine deiminase gene cluster reveals highly conserved non-coding segments and a new human gene, PADI6" Gene, 2004, 330:19–27.*

Hoppe et al., "High variablility of peptidylarginine deiminase 4 (PADI4) in a healthy white population:" Journal of Molecular Medicine, Aug. 25, 2004, online publication.*

Skolnick et al., "From genes to protein structure and function: novel applications of computational approaches in the genomic era", Trends in Biotechnology, 2000, 18(1):34–39.*

Colman, P.M. "effects of amino acid sequence changes on antibody–antigen interactions" Research in Immunology, 1994, 145:33–36.*

Naz, Rajesh K: "Application of Sperm Antigens in Immunocontraception", Frontiers in Bioscience 1, e87–95, Sep. 1 (1996).

Chen, Michellee S., et al.: "Role of the integrin–associated protein CD9 in binding between sperm ADAM 2 and the egg interin a6b1: Implications for Murine Fertilization", PNAS, vol. 96, No. 21, pp 11830–11835, Oct. 12, (1999).

Diekman, Alan B. et al,: "N–linked glycan of a sperm CD52 glycoform associated with human infertility", FASEB, vol. 13, pp 1303–1308, Aug. (1999).

Le Noir, Francois, et al.: "Severely Reduced Female Fertility in CD9–Defecient Mice", SCIENCE, vol. 287, Jan. 14 (2000), pp. 319–321.

Database EMBL 'Online!, Accession No. AU018623, Aug. 1, 1998, KO, M.S. et al: "Mus musculus 8–cell embryo cDNA 3'—end sequence, clone J0505G08".

Database EMBL 'Online, Accession No. C88186, Mar. 2, 1998, Doi, H. et al.: "Mus Musculus fertilized egg cDNA 3'end sequence, clone J0258C02".

Miyado, Kenji, et al.: "Reguirement of CD9 on the Egg Plasma Membrane for Fertilization", SCIENCE, vol. 287, Jan. 14, (2000), pp. 321–324.

* cited by examiner

Primary Examiner—Patrick J. Nolan
Assistant Examiner—Michael Szperka
(74) Attorney, Agent, or Firm—Rodney L. Sparks

(57) ABSTRACT

The present invention relates to proteins that are expressed in oocytes, nucleic acid sequences encoding those proteins and antibodies generated against those proteins. Composition and methods are provided for using the disclosed oocyte proteins as targets for contraceptive drugs.

3 Claims, 1 Drawing Sheet

EGG SPECIFIC SURFACE PROTEINS

This application is the national stage entry filed under 35 USC 371 of the international application PCT/US01/01718, filed Jan. 19, 2001, which claims benefit under 35 USC 119(e) of U.S. provisional application 60/177,123, filed Jan. 20, 2000. +gi

U.S. GOVERNMENT RIGHTS

This invention was made with United States Government support under Grant No. HD U54 29099, awarded by the National Institutes of Health. The United States Government has certain rights in the invention.

FIELD OF THE INVENTION

The present invention is directed to egg specific surface antigens that are involved in egg-sperm binding and fusion, and thus make suitable targets for producing antibodies which bind epitopes on the egg surface and modulate fertility. Methods are provided for the use of such antigens in methods for sterilization of female animals and generate antibodies useful for temporary, reversible contraception methods.

BACKGROUND OF THE INVENTION

There is increasing interest in developing an immunological approach to contraception for humans and sterilization for animal populations. A contraceptive vaccine would provide many advantages over currently available methods of contraception. Methods of contraception such as hormone therapies and chemical or mechanical barriers against fertilization have serious drawbacks, such as undesirable side effects and less than complete effectiveness. For example, side effects of hormonal therapies such as the pill include cancer, and in the case of mechanical barriers, increased susceptibility to infection. In addition, contraceptive vaccines would further be useful for fertility control of animal populations, where long-term or permanent sterilization, without the need for frequent intervention, is desirable. For example, such long-term sterilization would be useful for controlling fertility in human beings or agriculturally important livestock, such as cattle and pigs. Further, contraceptive vaccines would be useful for permanent sterilization regimes useful for pest control, such as for sterilization of rodents or other unwanted populations.

While there has been much interest in the development of immunocontraceptives, the focus has been, until recently, on the development of immunocontraceptives directed against sperm surface antigens, or on already known peptide hormones such as human chorionic gonadotropin and follicle stimulating hormone. One obstacle to the development of an effective egg surface antigen based immunocontraceptive vaccine has been the lack of knowledge regarding the molecular identities of egg surface proteins known to be directly involved in the fertilization process.

Mammalian fertilization may be defined as a series of gametic interactions in which capacitated sperm must first penetrate the cumulus cells and zona pellucida (the egg vestments), then bind to and fuse with the egg plasma membrane (oolemma). The initial binding event between gametes is known as primary binding and occurs, in the mouse model, when the zona pellucida protein, ZP3, binds to a receptor(s) on the sperm (reviewed in (McLeskey et al., 1998, Int. Rev. of Cytol. 177: 57–113). This binding event also initiates the acrosome reaction in which hydrolytic enzymes are released from the acrosomal compartment and act on the zona pellucida to facilitate penetration of the zona pellucida by sperm. Zona penetration is known as secondary binding and is mediated by the zona protein, ZP2, and one or more molecules on the inner acrosomal membrane (reviewed in Snell and White, 1996, Cell 85: 629–637).

Upon emergence from the zona pellucida, sperm then cross the perivitelline space and bind to and fuse with the oolemma. The molecular basis of sperm-oolemma binding and fusion has yet to be fully elucidated; however; recent evidence has demonstrated that integrins are involved in the interaction. Almeida et al. (1995, Cell 81:1095–1104) found that when oocytes were treated with monoclonal antibodies against the egg surface integrin $\alpha 6\beta 1$, mouse sperm-oolemma binding was reduced. Further, these investigators reported that somatic cells which express $\alpha 6\beta 1$ bind mouse sperm avidly while somatic cells that lack $\alpha 6$ or $\beta 1$ do not. A proposed sperm surface ligand for $\alpha 6\beta 1$ is fertilin. Fertilin contains a domain homologous to a family of integrin ligands known as disintegrins (Blobel et al., 1992, Nature 356: 248–252), which suggest a cell adhesion function for the molecule. Also, recombinant fertilin is known to bind to the oolemma (Evans et al., 1997, Dev. Biol. 187:79–93), with both monoclonal antibodies to fertilin (Primakoff et al., 1987, J. Cell. Biol. 104: 141–149) and fertilin peptide analogs (Almeida et al., 1995, Cell 81: 1095–1104; Evans et al., 1995, J. Cell. Sci. 108: 3267–3278) blocking sperm-oolemma binding and fusion.

Sperm-egg binding and fusion is likely to require multiple receptor-ligand interactions and other oolemmal proteins are likely to be involved in the fertilization process. In fact, there is indirect evidence implicating other oolemmal proteins in sperm-egg interaction. A purified sperm-associated protein (protein DE) which is involved in fusion in the rat, binds to the surface of zona-free rat oocytes (Cohen et al., 1996, Biol. Reprod. 55: 200–206). Another putative oolemmal sperm receptor is removed from the surface of radioiodinated mouse eggs following trypsin treatment and reappears on the egg surface after 3–6 h of culture (Kellom et al., 1992, Mol. Reprod. Dev. 33: 46–52). The reappearance of this 94 kDa protein on the egg surface coincides with the ability of the trypsin-treated eggs to be penetrated by sperm.

Glycosyl-phosphatidylinositol (GPI)-anchored proteins may play a key role in gamete interaction. GPI-anchored proteins possess a covalently linked glycosylated phosphatidylinositol moiety which serves to attach the protein portion of the molecule to the cell surface lipid bilayer (Low and Saltiel, 1988, Science, 239: 268–275). Proteins linked to the cell surface via a phosphatidylinositol anchor are known to be involved in a wide variety of cellular functions including T cell activation, hydrolysis of extracellular matrix proteins, transduction of extracellular stimuli, and cell-cell adhesion (reviewed in Low and Saltiel, 1988, Science, 239: 268–275). GPI-anchored proteins can be released from the cell surface by treatment of cells with the highly specific enzyme phosphatidylinositol-specific phospholipase C (PI-PLC) (Low and Finean, 1978, Bioch. Biophys. Acta. 508: 565–570). Therefore, treatment of intact cells with PI-PLC has become a useful tool to characterize the released proteins and to investigate the role of GPI-anchored proteins in cell function.

The hamster oocyte is unique in that zona-free eggs from other species such as the mouse, rat, and guinea pig do not incorporate heterologous sperm as readily (Yanagimachi, 1972, J. Reprod. Fertil., 28: 477–480; Hanada and Chang, 1976, J. Reprod. Fertil., 46: 239–241; and Quinn, 1979, 210: 497–506). Because of this promiscuity, the zona-free hamster egg has been used extensively in the sperm penetration assay (SPA) to assess the fertilizing capacity of human spermatozoa (Yanagimachi et al., 1976, Biol. Reprod., 15: 471–476; Rodgers et al., 1979; Liu and Baker, 1992, Fertil. Steril., 59: 698–699). In spite of the widespread use of this assay, the molecular interactions which occur between the human sperm and hamster oocyte during gamete interaction remain largely unknown. Presumably, however, there are molecules on the hamster egg plasma membrane (oolemma) which specifically interact with molecules on the human sperm plasma membrane during sperm-egg binding and fusion.

There have been a number of recent attempts to produce contraceptive vaccines directed against egg antigens (U.S. Pat. Nos. 5,820,863, 5,641,487, 5,637,300, and 4,996,297). To date, because of their relative abundance and accessibility to immunodetection, the focus has been on identifying zona pellucida epitopes. However, results from fertility trials in several species have shown that ovarian histopathology is often observed in ZP3 immunized animals. Therefore, commercial contraceptive companies have lost interest in zona proteins as contraceptive immunogens.

A new approach for an effective contraceptive vaccine that specifically targets antigens directly involved in the fertilization process is needed. However, to date, there are no reports of vaccines directed against egg protein(s) directly involved in the process of sperm-egg fusion step which is required for fertilization. The present invention is directed to contraceptive compositions and methods that are based on egg specific surface proteins.

Definitions

In describing and claiming the invention, the following terminology will be used in accordance with the definitions set forth below.

As used herein, "nucleic acid," "DNA," and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention.

The term "peptide" encompasses a sequence of 3 or more amino acids wherein the amino acids are naturally occurring or synthetic (non-naturally occurring) amino acids. Peptide mimetics include peptides having one or more of the following modifications:

1. peptides wherein one or more of the peptidyl —C(O)NR— linkages (bonds) have been replaced by a non-peptidyl linkage such as a —CH$_2$-carbamate linkage (—CH$_2$OC(O)NR—), a phosphonate linkage, a —CH$_2$-sulfonamide (—CH$_2$—S(O)$_2$NR—) linkage, a urea (—NHC(O)NH—) linkage, a —CH$_2$-secondary amine linkage, or with an alkylated peptidyl linkage (—C(O)NR—) wherein R is C$_1$–C$_4$ alkyl;
2. peptides wherein the N-terminus is derivatized to a —NRR$_1$ group, to a —NRC(O)R group, to a —NRC(O)OR group, to a —NRS(O)$_2$R group, to a —NHC(O)NHR group where R and R$_1$ are hydrogen or C$_1$–C$_4$ alkyl with the proviso that R and R$_1$ are not both hydrogen;
3. peptides wherein the C terminus is derivatized to —C(O)R$_2$ where R$_2$ is selected from the group consisting of C$_1$–C$_4$ alkoxy, and —NR$_3$R$_4$ where R$_3$ and R$_4$ are independently selected from the group consisting of hydrogen and C$_1$–C$_4$ alkyl.

Naturally occurring amino acid residues in peptides are abbreviated as recommended by the IUPAC-IUB Biochemical Nomenclature Commission as follows: Phenylalanine is Phe or F; Leucine is Leu or L; Isoleucine is Ile or I; Methionine is Met or M; Norleucine is Nle; Valine is Vat or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; Glycine is Gly or G, and X is any amino acid. Other naturally occurring amino acids include, by way of example, 4-hydroxyproline, 5-hydroxylysine, and the like.

Synthetic or non-naturally occurring amino acids refer to amino acids which do not naturally occur in vivo but which, nevertheless, can be incorporated into the peptide structures described herein. The resulting "synthetic peptide" contain amino acids other than the 20 naturally occurring, genetically encoded amino acids at one, two, or more positions of the peptides. For instance, naphthylalanine can be substituted for trytophan to facilitate synthesis. Other synthetic amino acids that can be substituted into peptides include L-hydroxypropyl, L-3,4-dihydroxyphenylalanyl, alpha-amino acids such as L-alpha-hydroxylysyl and D-alpha-methylalanyl, L-alpha.-methylalanyl, beta.-amino acids, and isoquinolyl. D amino acids and non-naturally occurring synthetic amino acids can also be incorporated into the peptides. Other derivatives include replacement of the naturally occurring side chains of the 20 genetically encoded amino acids (or any L or D amino acid) with other side chains.

As used herein, the term "conservative amino acid substitution" are defined herein as exchanges within one of the following five groups:

I. Small Aliphatic, Nonpolar or Slightly Polar Residues:
   Ala, Ser, Thr, Pro, Gly;
II. Polar, Negatively Charged Residues and Their Amides:
   Asp, Asn, Glu, Gln;
III. Polar, Positively Charged Residues:
   His, Arg, Lys;
IV. Large, Aliphatic, Nonpolar Residues:
   Met Leu, Ile, Val, Cys
V. Large, Aromatic Residues:
   Phe, Tyr, Trp As used herein, the term "purified" and like terms relate to the isolation of a molecule or compound in a form that is substantially free of contaminants normally associated with the molecule or compound in a native or natural environment.

As used herein, the term "MOP5 polypeptide" and like terms refers to polypeptides comprising SEQ ID NO: 2 and biologically active fragments thereof.

As used herein, the term "MOP8 polypeptide" and like terms refers to polypeptides comprising SEQ ID NO: 4 and biologically active fragments thereof.

As used herein, the term "biologically active fragments" or "bioactive fragment" of an egg surface polypeptide encompasses natural or synthetic portions of the native peptide that are capable of specific binding to at least one of the natural ligands of the respective native MOP5 or MOP8 polypeptide.

"Operably linked" refers to a juxtaposition wherein the components are configured so as to perform their usual function. Thus, control sequences or promoters operably linked to a coding sequence are capable of effecting the expression of the coding sequence.

As used herein, the tern "pharmaceutically acceptable carrier" encompasses any of the standard pharmaceutical carriers, such as a phosphate buffered saline solution, water and emulsions such as an oil/water or water/oil emulsion, and various types of wetting agents.

SUMMARY OF THE INVENTION

The present invention is directed to egg plasma membrane antigens useful for producing antibodies which will bind epitopes on the egg surface and modulate fertilization. The invention further encompasses compositions and methods for immunizing an individual for production of antibodies against egg surface antigen(s). Methods are also provided for the use of antibodies against such antigens for active immunization, or sterilization, of female animals, by induction of a T-cell attack on the egg. These methods are particularly useful in cases where permanent sterilization is desired, for example, for sterilization of animal populations. Methods are further provided for the use of egg surface antigens to generate antibodies useful for passive immunization that can be used for reversible contraception methods.

DETAILED DESCRIPTION OF THE INVENTION

The present invention relates to identification of antigens that are expressed predominantly in eggs. These proteins can be used as immunogens in a vaccine preparation to aid in the modulation of fertility. Described in detail below are the egg surface antigens, methods for their production, and methods for their use to modulate fertility.

Isolation of MOP5

Autoimmune Premature ovarian failure affects 1% of women in the US. The disease is characterized by infiltration of leucocytes and antibodies into the ovary resulting in loss of ovarian function. Symptoms of the disease include infertility, amenorrhea, and autoimmune oophoritis. A similar disease can be induced in mice by neonatal thymectomy. Accordingly, antisera from thymectomized mice can be used to identify the key oocyte antigens that are targeted in Autoimmune Premature Ovarian Failure and thus identify key proteins for oocyte function. Antibodies in sera from thymectomized mice recognizes a limited number of egg antigens as detected by western blots of 2D gels of mouse oocyte proteins.

Sera from thymectomized mice specifically reacts with three different mouse oocyte proteins: MW~76, 90, and 125 kDA. A protein approximately 73.5 kDa and pI of 5.39 (and recognized by sera from thymectomized mice) was cored from a 2D gels of mouse oocyte proteins and designated MOP5. This protein was subjected to Tandem Mass Spectroscopic Analysis and peptide sequences were obtained. One peptide (VCGXXE; SEQ ID NO: 6) matched a mouse EST and this EST was used to design primers for use in 5' and 3' PCR RACE reactions to clone the MOP5 cDNA sequence.

Figure 1:
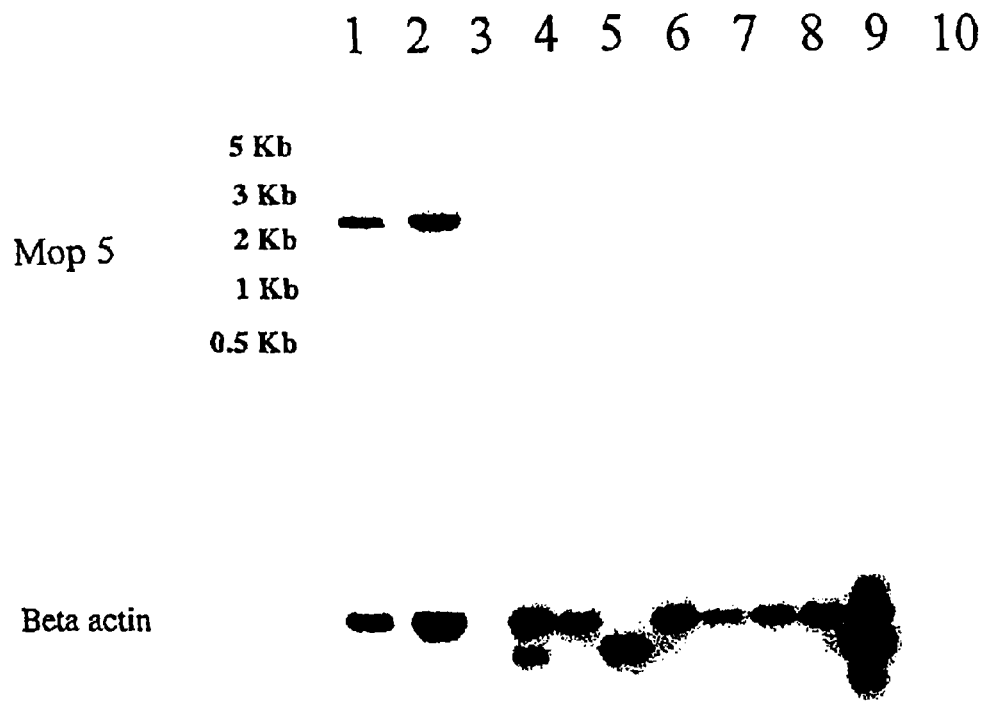
FIG. 1 is a copy of a multiple tissue Northern Blot, wherein MOP5 cDNA was radiolabeled with $P^{32}$ and hybridized to 2 ug poly-(A)+ mRNAs, revealing a prevalent message in ovary RNA. The size of the molecular weight markers is indicated at the left; lanes 1–10 contain poly-(A)+ mRNA isolated from COC, ovary, heart, brain, spleen, lung, liver, small intestine, kidney and testis, respectively. The lower panel of FIG. 1 shows the identical blot probed with β-actin cDNA as a positive control.

The nucleic acid sequence of MOP5 is shown as SEQ ID NO: 1 and the deduced amino acid sequence is shown as SEQ ID NO: 2. The cDNA sequence is 2341 bp in length and includes a 99 bp 5' untranslated region, a 1995 bp open reading frame and a 247 bp 3' untranslated region. The coding region of MOP5 is shown as SEQ ID NO: 7. The entire cDNA sequence was used to probe a Northern blot containing poly-(A)+ mRNA isolated from COC, ovary, heart, brain, spleen, lung, liver, small intestine, kidney and testis. The cumulus oocyte complex (COC) lane represents mRNA isolated from ovulated eggs and includes support cells and tissues affiliated with recently ovulated eggs. The Northern blot demonstrates that MOP5 mRNA is abundantly expressed in the ovary (see FIG. 1). A longer exposure of the Northern blot revealed that MOP5 mRNA is also expressed in testes albeit at a much lesser extent. Accordingly, MOP5 is a gonad specific gene.

The deduced amino acid sequence of MOP5 is 664 amino acids in length with a predicted mass of 73.5 and pI of 5.39. The amino acid sequence of MOP5 is shown in SEQ ID NO: 2. Blast homology search demonstrates that MOP5 is most similar (40% identical, 60% positive, 5% gaps) to the peptidylarginine deiminase (PAD) family of enzymes. PADs are post-translation modification enzymes which convert arginine residues on proteins to citrulline residues in the presence of calcium. Known substrates for PAD include: filaggrin (epithelial cells), trichohyalin (sheath protein of hair follicle), trypsin inhibitors, histones and protamine (salmon sperm). Enzymatic deimination changes the functional properties of proteins due to decrease in net charge resulting in protein unfolding MOP5's similarity to peptidylarginine deiminase implies that MOP5 functions in the unfolding of proteins in the gametes. Since histones are a substrate for PAD, MOP5 may interact specifically with gamete histones and be involved with decondensing the sperm nucleus upon fusion of the egg and sperm. Accordingly, agonists or antagonists of MOP5 could be used to treat fertility problems resulting from improper MOP5 activity, including for example failure to properly decondense sperm DNA. MOP5 could also play an active role in the activation of genes necessary for the viability of gametes. Accordingly, MOP5's role in unfolding proteins and regulating the transcription of genes could lead to therapies for treating diseases relating to overexpression or underexpression of gene products, including cancer.

In one embodiment, the present invention provides methods of screening for agents, small molecules, or proteins that interact with polypeptides comprising the sequence of SEQ ID NO: 2 or bioactive fragments thereof. The invention encompasses both in vivo and in vitro assays to screen small molecules, compounds, recombinant proteins, peptides, nucleic acids, antibodies etc. which bind to or modulate the activity of MOP5 and are thus useful as therapeutics or diagnostic markers for fertility.

CV-1 cells were transfected with Mop5-pCDNA3./Myc plasmid and recombinant MOP5 was expressed in tissue culture cells. A CV-1 cell lysate made with Tris-EDTA buffer and blotted and the subsequent Western blot probed with anti-Myc demonstrated that the protein was expressed.

MOP5 was also expressed in bacterial cells (BL21 cells) and the protein was purified and used to make antibodies in guinea pigs. In particular, monospecific polyclonal antibodies were generated against the N-terminal half of MOP5 expressed in BL21 bacteria. Zona-free oocytes fixed and permeabilized prior to treatment with antibody (1° Ab: 1:50 dilution of guinea pig sera, 2° Ab: 1:200 dilution FITC labeled D anti-Guinea Pig) showed that the MOP5 antibody recognizes a protein in the mouse oocyte.

Isolation of MOP8

A protein approximately 65 kDa and pI of 5.8 was cored from a coomassie stained 2D gels of mouse oocyte proteins (extracted from zona-free oocytes) and designated MOP8. MOP8 had been identified as a surface protein by surface labeling intact zona-free eggs prior to extracting the proteins. The MOP8 protein spot was subjected to Tandem Mass Spectroscopic Analysis and peptide sequences were obtained. One peptide (QDWDFHESNQK; SEQ ID NO: 5) matched a mouse EST and this EST was used to design primers for use in 5' and 3' PCR RACE reactions to clone the MOP8 cDNA sequence.

Figure 2:
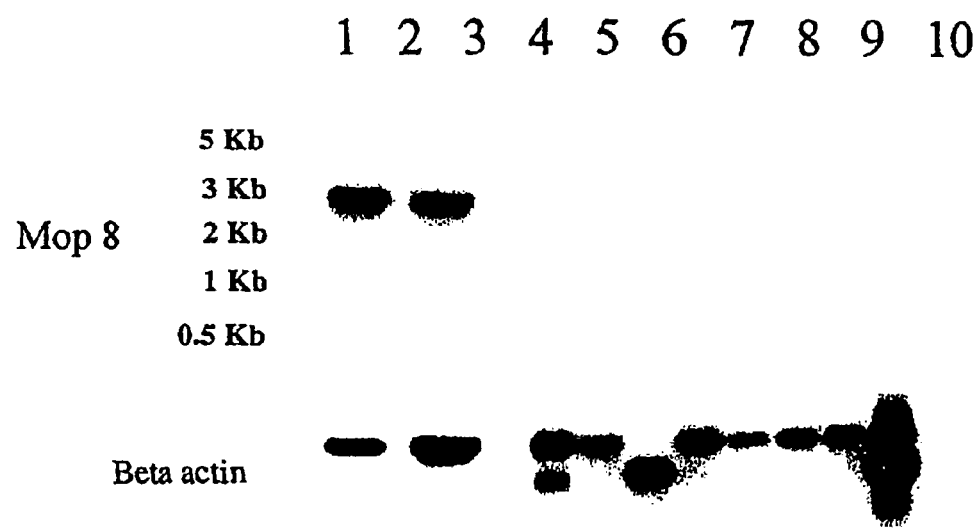
FIG. 2 is a copy of a multiple tissue Northern Blot, wherein MOP8 cDNA was radiolabeled with $P^{32}$ and hybridized to 2 ug poly-(A)+ mRNAs, revealing a message only in ovary RNA. The size of molecular weight markers is indicated at the left; lanes 1–10 contain poly-(A)+ mRNA isolated from COC, ovary, heart, brain, spleen, lung, liver, small intestine, kidney and testis, respectively. The lower panel of FIG. 2 shows the identical blot probed with μ-actin cDNA as a positive control.

The nucleic acid sequence of MOP8 is shown as SEQ ID NO: 3 and the deduced amino acid sequence is shown as SEQ ID NO: 4. The cDNA sequence is 2665 bp in length and includes a 75 bp 5' untranslated region, a 1794 bp open reading frame and a 796 bp 3' untranslated region. The entire cDNA sequence was used to probe a Northern blot containing poly-(A)+ mRNA isolated from COC, ovary, heart, brain, spleen, lung, liver, small intestine, kidney and testis. The Northern blot demonstrates the MOP5 mRNA is abundantly expressed only in the ovary (see FIG. 2).

The deduced amino acid sequence of MOP5 is 597 amino acids in length with a predicted mass of 67.8 kDa and pI of 5.7. The amino acid sequence of MOP5 is shown in SEQ ID NO: 4. Blast homology search demonstrates that MOP8 is most similar (56% identical, 70% positive, 5% gaps) to human cystolic phospholipase A2 gamma (cPLA2 g). Phospholipase A2 is known to cleave the sn-2 fatty acyl bond of phospholipids, producing a free arachadonic acid and a lysophospholipid. Arachadonic acid is the precursor of a large family of compounds known as the eicosanoids, which includes prostaglandins and leukotrienes. These molecules mediate a wide variety of functions including inflammatory reactions. A large number of different types of plasma membrane receptors, including many that act via heterotrimeric GTP-binding proteins or tyrosine kinases, have been demonstrated to induce activation of PLA2. There is considerable evidence in the literature that PLA2 is required for sperm-egg interaction, however the molecule has not been previously cloned in gametes. Accordingly, in accordance with one embodiment a composition is provided that interfere with the activity of MOP8 as a means of contraceptive. In accordance with one embodiment and antigenic composition is provided comprising a polypeptide that comprises the sequence of SEQ ID NO: 4 or an antigenic fragment of SEQ ID NO: 4. In one embodiment the antigenic composition is combined with a pharmaceutically acceptable carrier to form a contraceptive vaccine.

Since MOP8 is expressed only in ovary tissue, MOP8 is a novel ovary specific gene and not simply the mouse homologue of human cytosolic phospholipaseA2 gamma. Rather MOP8 is likely a novel oocyte-specific phospholipase A2 isoform.

The open reading frame of MOP8 has been cloned into the pcDNA3. 1/Myc (to createMOP8-pcDNA3/Myc) mammalian expression vector and the protein was expressed in CV-1 cells. Western blot analysis using an anti-Myc antibody demonstrates that rMOP8 localizes to the pellet fraction (100,000 g) indicating that the protein may be membrane associated.

MOP8 has also been expressed in bacterial cells (BL21 cells) and the protein has been purified. This purified protein will be used to make antibodies in guinea pigs. In particular, monospecific polyclonal antibodies were generated against the N-terminal half of MOP5 expressed in BL21 bacteria. Zona-free oocytes fixed and permeabilized prior to treatment with antibody (1° Ab: 1:50 dilution of guinea pig sera; 2° Ab: 1:200 dilution FITC labeled D anti-Guinea Pig) showed that the MOP5 antibody recognizes a protein in the mouse oocyte.

In accordance with one embodiment of the present invention, an egg surface protein, its fragments or other derivatives, or analogs thereof, are used as an immunogen to generate antibodies which immunospecifically bind such an immunogen. In particular, polypeptides comprising the amino acid sequence of SEQ ID NO: 2 or SEQ ID NO: 4, or antigenic fragments of those polypeptides are used to formulate immunogenic formulations.

In one embodiment, the present invention provides methods of screening for agents, small molecules, or proteins that interact with the polypeptides of SEQ ID NO: 2 or SEQ ID NO: 4 or binding domain-containing fragments of SEQ ID NO: 2 or SEQ ID NO: 4. The invention encompasses both in vivo and in vitro assays to screen small molecules, compounds, recombinant proteins, peptides, nucleic acids, antibodies etc. which bind to or modulate the activity of C19 or C23 and are thus useful as therapeutics or diagnostic markers for fertility.

For example, polypeptides comprising SEQ ID NO: 2 or SEQ ID NO: 4, or a bioactive fragment thereof, can be used to isolate ligands that bind to the respective native polypeptide under physiological conditions. The method comprises the steps of contacting the MOP5 or MOP8 polypeptide with a mixture of compounds under physiological conditions, removing unbound and non-specifically bound material, and isolating the compounds that remain bound to the MOP5 or MOP8 polypeptide. Typically, the MOP5 or MOP8 polypeptide will be bound to a solid support using standard techniques to allow rapid screening compounds. The solid support can be selected from any surface that has been used to immobilize biological compounds and includes but is not limited to polystyrene, agarose, silica or nitrocellulose. In one embodiment the solid surface comprises functionalized silica or agarose beads. Screening for such compounds can be accomplished using libraries of pharmaceutical agents and standard techniques known to the skilled practitioner.

In one embodiment, the present invention is directed to a purified polypeptide comprising the amino acid sequence of SEQ ID NO: 2, or an amino acid sequence that differs from SEQ ID NO: 2 by one or more conservative amino acid substitutions. More preferably, the purified polypeptide comprises an amino acid sequence that differs from SEQ ID NO: 2 by 10 or less conservative amino acid substitutions. Alternatively, the polypeptide may comprise an amino acid sequence that differs from SEQ ID NO: 2 by 1 to 3 alterations, wherein the alterations are independently selected from a single amino acid deletion, insertion or substitution.

Another embodiment of the present invention is directed to a purified polypeptide comprising the amino acid sequence of SEQ ID NO: 4, or an amino acid sequence that differs from SEQ ID NO: 4 by one or more conservative amino acid substitutions. More preferably, the purified polypeptide comprises an amino acid sequence that differs from SEQ ID NO: 4 by 10 or less conservative amino acid substitutions. Alternatively, the polypeptide may comprise an amino acid sequence that differs from SEQ ID NO: 4 by 1 to 3 alterations, wherein the alterations are independently selected from a single amino acid deletion, insertion or substitution.

Another embodiment of the present invention encompasses polypeptides comprising a fragment of SEQ ID NO: 2 and SEQ ID NO: 4, wherein the peptide fragment is at least ten amino acids in length and comprises ten contiguous amino acids that are identical in sequence to an ten contiguous amino portion of SEQ ID NO: 2 or SEQ ID NO: 4.

The present invention also encompasses antibodies, including anti-idiotypic antibodies, antagonists and agonists, as well as compounds or nucleotide constructs that inhibit expression of the MOP5 or MOP8 genes (transcription factor inhibitors, antisense and ribozyme molecules, or gene or regulatory sequence replacement constructs), or promote expression of MOP5 or MOP8 (e.g., expression constructs in which C19 or C23 coding sequences are operatively associated with expression control elements such as promoters, promoter/enhancers, etc.). Antibodies against the MOP5 or MOP8 polypeptides can be used for the diagnosis of conditions or diseases characterized by expression or overexpression of MOP5 or MOP8, or in assays to monitor patients being treated with MOP5 or MOP8 agonists, antagonists or inhibitors.

In accordance with one embodiment, antibodies are provided that specifically bind to MOP5 or MOP8. In particular, a MOP5 or MOP8 polypeptide, or analogs thereof, may be used as an immunogen to generate antibodies which immunospecifically bind such an immunogen. In accordance with one embodiment of the preset invention an antigenic compound is provided for generating antibodies, wherein the compound comprises an amino acid sequence selected from the group consisting of SEQ ID NO: 2 or SEQ ID NO: 4. The antibodies generated can be formulated with standard carriers and optionally labeled to prepare therapeutic or diagnostic compositions. Antibodies to MOP5 or MOP8 may be generated using methods that are well known in the art.

Antibodies raised against MOP5 and MOP8 include but are not limited to polyclonal, monoclonal, chimeric, single chain, Fab fragments, and an Fab expression library. In a specific embodiment, antibodies to a human egg surface protein are produced. In another embodiment, antibodies to a domain (e.g., the extracelluar domain released by treatment with PI-PLC) of an egg surface protein are produced. In a specific embodiment, fragments of an egg surface protein, such as MOPS or MOP8, that are identified as hydrophilic regions are used as immunogens for antibody production.

Various procedures known in the art may be used for the production of polyclonal antibodies to an egg surface protein or derivative or analog thereof. In a particular embodiment, rabbit polyclonal antibodies to an epitope of an egg surface protein or fragment, can be obtained. For the production of antibody, various host animals, including but not limited to rabbits, mice, rats, etc can be immunized by injection with the native egg surface proteins, or a synthetic version, or derivative (e.g., fragment) thereof. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

For preparation of monoclonal antibodies directed toward an egg surface protein sequence or analog thereof, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in *Monoclonal Antibodies and Cancer Therapy*, Alan R. Liss, pp. 77–96). In fact, according to the invention, techniques developed for the production of "chimeric antibodies" (Morrison et al., 1984, Proc. Natl. Acad. Sci. U.S.A. 81:6851–6855; Neuberger et al., 1984, Nature 312:604–608; Takeda et al., 1985, Nature 314:452–454) by splicing the genes from a mouse antibody molecule specific for egg surface proteins together with genes from a human antibody molecule of appropriate biological activity can be used; such antibodies are within the scope of this invention.

According to the present invention, techniques described for the production of single chain antibodies (U.S. Pat. No. 4,946,778) can be adapted to produce egg surface protein-specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity for egg surface proteins, derivatives, or analogs.

Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, the Fab fragments which can be generated by treating the antibody molecule with papain and a reducing agent, and Fv fragments.

In the production of antibodies, screening for the desired antibody can be accomplished by techniques known in the art, e.g. ELISA (enzyme-lied immunosorbent assay). For example, to select antibodies which recognize a specific domain of an egg surface protein, one may assay generated hybridomas for a product which binds to an egg surface protein fragment containing such domain. For selection of an antibody that specifically binds a first egg surface protein homolog but which does not specifically bind a different egg surface protein homolog, one can select on the basis of positive binding to the first egg surface protein homolog and a lack of binding to the second egg surface protein homolog. Antibodies specific to a domain of an egg surface proteins are also provided.

The foregoing antibodies can be used in methods known in the art relating to the localization and activity of the egg surface proteins of the invention, e.g., for imaging these proteins, measuring levels thereof in appropriate physiological samples, in diagnostic methods, etc.

The antibodies generated against the MOP5 and MOP8 antigens also have potential uses in vaccination against fertilization, sterilization, diagnostic immunoassays, passive immunotherapy, and generation of antiidiotypic antibodies. For example, antibodies may be isolated by standard techniques known in the art (e.g., immunoaffinity chromatography, centrifugation, precipitation, etc.) and used in diagnostic immunoassays. The antibodies may also be used to monitor treatment and/or disease progression. Any immunoassay system known in the art, such as those listed supra, may be used for this purpose including but not limited to competitive and noncompetitive assay systems using techniques such as radioimmunoassays, ELISA (enzyme-linked immunosorbent assays), "sandwich" immunoassays, precipitin reactions, gel diffusion precipitin reactions, immunodiffusion assays, agglutination assays, complement-fixation assays, immunoradiometric assays, fluorescent immunoassays, protein A immunoassays and immunoelectrophoresis assays, to name but a few.

The vaccine formulations of the present invention can also be used to produce antibodies for use in passive immunotherapy, in which short-term protection of a host is achieved by the administration of pre-formed antibody directed against a heterologous organism.

The antibodies generated by the vaccine formulations of the present invention can also be used in the production of antiidiotypic antibody. The antiidiotypic antibody can then in turn be used for immunization, in order to produce a subpopulation of antibodies that bind the initial antigen of the pathogenic microorganism (Jerne, 1974, Ann. Immunol. (Paris) 125c:373; Jerne, et al., 1982, EMBO J. 1:234).

In another embodiment of the invention egg specific surface polypeptides, and fragments thereof containing the extracellular domain, are useful contraceptive vaccines. In accordance with one embodiment a vaccine composition is provided wherein the composition comprises an amino acid sequence selected from the group consisting of SEQ ID NO: 2, SEQ ID NO: 4 and antigenic fragments of SEQ ID NO: 2, SEQ ID NO: 4. The vaccines of the invention may be multivalent or univalent. Multivalent vaccines are made from recombinant viruses that direct the expression of more than one antigen.

In one aspect of the invention, MOP5 and MOP8 polypeptides (either separately or in combination) are delivered to a subject to elicit an active immune response. The vaccine acts as a temporary and reversible antagonist of the function of the egg surface proteins of the invention. For example, such vaccines could be used for active immunization of a subject, to raise an antibody response to temporarily block the sperm's access to the egg plasma antigen. In one aspect of the invention, an antigen could be administered at a certain period of the month, for example during ovulation of a female subject to block fertilization.

In another aspect of the invention, MOP5 and MOP8 polypeptides (either separately or in combination) are used as vaccines for permanent sterilization of a subject. Such vaccines can be used to elicit a T-cell mediated attack on the eggs, having an othoritic effect, useful as a method for irreversible sterilization. Methods for generating T-cell specific responses, such as adoptive immunotherapy, are well known in the art (see, for example, Vaccine Design, Michael F. Powell and Mark J. Newman Eds., Plenum Press, New York, 1995, pp 847–867). Such techniques may be particular useful for vetinary contraceptive or sterilization purposes, where a single dose vaccination may be desirable.

Suitable preparations of vaccines include injectables, either as liquid solutions or suspensions; solid forms suitable for solution in, suspension in, liquid prior to injection, may also be prepared. The preparation may also be emulsified, or the polypeptides encapsulated in liposomes. The active immunogenic ingredients are often mixed with excipients which are pharmaceutically acceptable and compatible with the active ingredient. Suitable excipients are, for example, water saline, dextrose, glycerol, ethanol, or the like and combinations thereof. In addition, if desired, the vaccine preparation may also include minor amounts of auxiliary substances such as wetting or emulsifying agents, pH buffering agents, and/or adjuvants which enhance the effectiveness of the vaccine.

Examples of adjuvants which may be effective, include, but are not limited to: mineral gels, e.g., aluminum hydroxide, surface active substances such as lysolecithin, pluronic polyols; polyanions; peptides; oil emulsions; alum, and MDP; N-acetyl-muramyl-L-threonyl-D-isoglutamine (thr-MDP), N-acetyl-nor-muramyl-L-alanyl-D-isoglutamine, N-acetyl-muramyl-L-alanyl-D-isoglutaminyl-L-alanine-2-(1'-2'-dipalmitoyl-sn-glycero-3-hydroxyphosphoryloxy)-ethylamine, aluminum hydroxide;.

The effectiveness of an adjuvant may be determined by measuring the induction of antibodies directed against an immunogenic polypeptide containing an egg surface protein polypeptide epitope, the antibodies resulting from administration of this polypeptide in vaccines which are also comprised of the various adjuvants. Effective doses (immunizing amounts) of the vaccines of the invention may also be extrapolated from dose-response curves derived from animal model test systems.

The polypeptides may be formulated into the vaccine as neutral or salt forms. Pharmaceutically acceptable salts include the acid addition salts (formed with free amino groups of the peptide) and which are formed with inorganic acids, such as, for example, hydrochloric or phosphoric acids, or organic acids such as acetic, oxalic, tartaric, maleic, and the like. Salts formed with free carboxyl groups may also be derived from inorganic bases, such as, for example, sodium potassium, ammonium, calcium, or ferric hydroxides, and such organic bases as isopropylamine, trimethylamine, 2-ethylamino ethanol, histidine, procaine and the like.

The present invention provides a method of immunizing an animal, comprising administering to the animal an effective immunizing dose of a vaccine of the present invention. The patient to which the vaccine is administered is preferably a mammal, most preferably a human, but can also be a non-human animal including but not limited to cows, horses, sheep, pigs, fowl (e.g., chickens), goats, cats, dogs, hamsters, mice and rats.

The vaccine formulations of the invention comprise an effective immunizing amount of the egg surface protein and a pharmaceutically acceptable carrier or excipient. Vaccine preparations comprise an effective immunizing amount of one or more antigens and a pharmaceutically acceptable carrier or excipient. Pharmaceutically acceptable carriers are well known in the art and include but are not limited to saline, buffered saline, dextrose, water, glycerol, sterile isotonic aqueous buffer, and combinations thereof. One example of such an acceptable carrier is a physiologically balanced culture medium containing one or more stabilizing agents such as stabilized, hydrolyzed proteins, lactose, etc.

The carrier is preferably sterile. The formulation should suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

Generally, the ingredients are supplied either separately or mixed together in unit dosage form, for example, as a dry lyophilized powder or water free concentrate in a hermetically sealed container such as an ampoule or sachette indicating the quantity of active agent. Where the composition is administered by injection, an ampoule of sterile diluent can be provided so that the ingredients may be mixed prior to administration.

The precise dose of vaccine preparation to be employed in the formulation will also depend on the route of administration, and the nature of the patient, and should be decided according to the judgment of the practitioner and each patient's circumstances according to standard clinical techniques. An effective immunizing amount is that amount sufficient to produce an immune response to the antigen in the host to which the vaccine preparation is administered.

The immunogen may also be incorporated into liposomes, or conjugated to polysaccharides and/or other polymers for use in a vaccine formulation. In instances where the recombinant antigen is a hapten, i.e., a molecule that is antigenic in that it can react selectively with cognate antibodies, but not immunogenic in that it cannot elicit an immune response, the hapten may be covalently bound to a carrier or immunogenic molecule; for instance, a large protein such as serum albumin will confer immunogenicity to the hapten coupled to it. The hapten-carrier may be formulated for use as a vaccine.

The present invention also encompasses nucleic acid sequences that encode the MOP5 and MOP8 polypeptides, bioactive fragments and derivatives thereof. In particular the present invention is directed to nucleic acid sequences comprising the sequence of SEQ ID NO: 1, or SEQ ID NO: 3, or fragments thereof. In one embodiment, purified nucleic acids comprising at least 20 contiguous nucleotides (i.e., a hybridizable portion) that are identical to any 20 contiguous nucleotides of SEQ ID NO: 1 or SEQ ID NO: 3 are provided. In other embodiments, the nucleic acids comprises at least 25 (contiguous) nucleotides, 50 nucleotides, 100 nucleotides, or 200 nucleotides of SEQ ID NO: 1 or SEQ ID NO: 3.

One embodiment of the present invention includes nucleic acids that hybridize (under conditions defined herein) to all or a portion of the nucleotide sequence represented by SEQ ID NO: 1 or its complement. Alternatively, the present invention also includes nucleic acids that hybridize (under conditions defined herein) to all or a portion of the nucleotide sequence represented by SEQ ID NO: 3 or its complement. The hybridizing portion of the hybridizing nucleic acids is typically at least 15 (e.g., 20, 25, 30, or 50) nucleotides in length. Hybridizing nucleic acids of the type described herein can be used, for example, as a cloning probe, a primer (e.g., a PCR primer), or as a diagnostic probe. The DNA sequence of SEQ ID NO: 1, SEQ ID NO: 3, or fragments thereof, can be used as probes to detect homologous genes from other vertebrate species.

Nucleic acid duplex or hybrid stability is expressed as the melting temperature or Tm, which is the temperature at which a nucleic acid duplex dissociates into its component single stranded DNAs. This melting temperature is used to define the required stringency conditions. Typically a 1% mismatch results in a 1° C. decrease in the Tm, and the temperature of the final wash in the hybridization reaction is reduced accordingly (for example, if two sequences having >95% identity, the final wash temperature is decreased from the Tm by 5° C.). In practice, the change in Tm can be between 0.5° C. and 1.5° C. per 1% mismatch.

The present invention is directed to a nucleic acid sequence comprising a sequence selected from the group consisting of SEQ ID NO: 1, SEQ ID NO: 3, SEQ ID NO: 7 and nucleic acid sequences that hybridize to those sequences (or fragments thereof) under stringent or highly stringent conditions. In one embodiment the nucleic acid sequence is at least 100 nucleotides in length and hybridizes to SEQ ID NO: 1 or SEQ ID NO: 3 under stringent or highly stringent conditions. In accordance with the present invention highly stringent conditions are defined as conducting the hybridization and wash conditions at no lower than −5° C. Tm. Stringent conditions are defined as involve hybridizing at 68° C. in 5×SSC/5× Denhardt's solution/1.0% SDS, and washing in 0.2×SSC/0.1% SDS at 68° C. Moderately stringent conditions include hybridizing at 68° C. in 5×SSC/5× Denhardt's solution/1.0% SDS and washing in 3×SSC/0.1% SDS at 42° C. Additional guidance regarding such conditions is readily available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10.

In another embodiment of the present invention, nucleic acid sequences encoding the MOP5 or MOP8 polypeptides can be inserted into expression vectors and used to transfect cells to enhance the expression of those proteins on the target cells. In accordance with one embodiment, nucleic acid sequences encoding MOP5 or MOP8, or a fragment or a derivative thereof, are inserted into a eukaryotic expression vector in a manner that operably links the gene sequences to the appropriate regulatory sequences, and recombinant MOP5 or recombinant MOP8 is expressed in a eukaryotic host cell. Suitable eukaryotic host cells and vectors are known to those skilled in the art. In particular, nucleic acid sequences encoding MOP5 or MOP8 may be added to a cell or cells in vitro or in vivo using delivery mechanisms such as liposomes, viral based vectors, or microinjection. Accordingly, one aspect of the present invention is directed to transgenic cell lines that contain recombinant genes that express MOP5 or MOP8.

EXAMPLE 1

Isolation of MOP5

For analytical two-dimensional electrophoresis the detergent/urea extracted zona-free mouse oocyte proteins from 2850 oocytes were separated by isoelectric focusing (IEF) in acrylamide tube gels prior to second dimensional gel electrophoresis (SDS-PAGE), which was performed in a Protean II xi Multi-Cell apparatus (Bio-Rad, Richmond, Calif.) or on large format (23×23 cm) gels (Investigator 2-D Electrophoresis System, ESA) which were also employed for preparative 2D gel electrophoresis. The immobilized proteins were visualized by staining in a solution containing 0.1% Commassie R250, 40% methanol and 0.1% acetic acid for one minute, followed by destaining in a solution of 10% acetic acid and 50% methanol for 3×3 minutes. The MOP5 spot was identified as a protein that is recognized by sera from mice who thymus gland has been removed.

The MOP5 spot was excised from a Coomassie stained 2-D gel and microsequenced using tandem mass spectrometry. One peptide (VCGXXE; SEQ ID NO: 6) matched a mouse EST and this EST was used to design primers for use in 5' and 3' PCR RACE reactions to clone the MOP5 cDNA sequence. The nucleic acid sequence of MOP5 is shown as SEQ ID NO: 1 and the deduced amino acid sequence is shown as SEQ ID NO: 2.

EXAMPLE 2

Isolation of MOP8

Solubilization and Electrophoresis of Human Spermatozoal Proteins

For analytical two-dimensional electrophoresis the detergent/urea extracted zona-free mouse oocyte proteins were separated by isoelectric focusing (IEF) in acrylamide tube gels prior to second dimensional gel electrophoresis (SDS-PAGE), which was performed in a Protean II xi Multi-Cell apparatus (Bio-Rad, Richmond, Calif.) or on large format (23×23 cm) gels (Investigator 2-D Electrophoresis System, ESA) which were also employed for preparative 2D gel electrophoresis. The immobilized proteins were visualized by staining in a solution containing 0.1% Commassie R250, 40% methanol and 0.1% acetic acid for one minute, followed by destaining in a solution of 10% acetic acid and 50% methanol for 3×3 minutes.

To determine if MOP8 is an egg surface protein, freshly harvested zona-free mouse oocytes were vectorially labeled with sulfo-NHS-LC biotin and separated by 2-D gel electrophoresis. Protein spots labeled with biotin were visualized by avidin-ECL and compared to a silver stained companion gel to identify the biotinylated protein spots. The 2D gels indicated that MOP8 is vectorially labeled with sulfo-NHS-LC biotin, and thus MOP8 is probably located on the surface of the sperm.

The MOP8 spot, having a mass of about 65 kDa and a pI of about 5.8, was excised from a Coomassie stained 2-D gel and microsequenced using tandem mass spectrometry. Twenty one peptide sequences were isolated, one of which (QDWDFHESNQK; SEQ ID NO: 5) matched a mouse expressed sequence tag. Data base search analysis done using the tryptic peptides revealed no matches to any known proteins. The mouse EST was used to design primers for use in 5' and 3' PCR RACE reactions to clone the MOP8 gene. The nucleic acid sequence of MOP8 is shown as SEQ ID NO: 3 and the deduced amino acid sequence is shown as SEQ ID NO: 4.

What is claimed is:

1. A purified polypeptide wherein the polypeptide comprises the amino acid sequence of SEQ ID NO: 2.

2. A nucleic acid sequence comprising a recombinant gene wherein said gene comprises the sequence of SEQ ID NO: 7 operably linked to control sequences.

3. A transgenic host cell comprising the nucleotide sequence of claim 2.

* * * * *

SEQUENCE LISTING

<160> NUMBER OF SEQ ID NOS: 7

<210> SEQ ID NO 1
<211> LENGTH: 2341
<212> TYPE: DNA
<213> ORGANISM: Mus musculus

<400> SEQUENCE: 1

```
gggtaaggac tgctgacagt ggctagcttg gtaagcccag ccatgtcttt tcagaactca      60
ctcagcctgt ctctggtcaa tcccacccat gccctctgca tggtaggcat ggaaatcacc     120
ttggacatca gcaagtgtgc accggacaag tgcaagtctt tcaccatccg tggttccccc     180
aggatcttga tccacatctc tagctccgtc atcgctggca aagaggacac tgtggtctgg     240
aggtcaatga accatcccac agtggcattg gtgaggatgg tggcgcccag ccccactgtg     300
gatgaagaca aggtgctggt ctcctacttc tgtcctgacc aagaagtccc cacggccaca     360
gctgtgctgt ttctcaccgg catcgagatc tccctggagg cagacatcta tcgagatgga     420
caactggaca tgccaagtga taagcaagct aagaaaaaat ggatgtgggg tatgaacggc     480
tggggagcca tcctgcttgt gaattgtagc cctaatgctg tgggccagcc tgatgaacag     540
tcctttcagg agggccccag agaaatacag aacaacctgt ctcagatgaa tgtaactgtg     600
gagggcccca ccagcatcct acagaattac cagttgatcc tacataccta cgaagaagag     660
gcgaagaaga caagagtcta ctggtctcag agaggctcct ctgcgtatga actggtggtg     720
ggacccaaca agcctgtcta tctcctgcct acctttgaga accgtaggaa agaggctttc     780
tacgtagaag ccacggaatt cccatctccc agcttctcgg gcctgatctc cttgtcactc     840
tccctagtag aaaaggctca cgacgagtgc atcccagaga ttccgctcta taaggataca     900
gtgatgttcc gggtggcacc ttatatcttc atgcccagca cccagatgcc tctagaggtt     960
tacctgtgca gggagctaca gctgcaaggc tttgtggact cagtgaccaa gctgagcgag    1020
```

```
aagagcaaag tgcaggtggt aaaggtctat gaggacccca accgccagag caagtggctc      1080
caggacgaga tggctttctg ctatactcag gctcctcaca agacggtgtc attgatcctt      1140
gacaccccaa gggtttccaa gctggaagac ttccccatga atacacact gaccctggc        1200 tctggctacc tgatccgaca aattgaggac caccggggtgg ctagcctgga ttccatcggg     1260
aacctgatgg tatctccgcc tgtcaaggct cagggcaaag actaccctct agggaggggtc     1320 ctcattggtg gcagctttta ccccagctct gagggccggg acatgaacaa gggcctgcga      1380
gaattcgtgt atgcccagca ggtgcaggcc cctgtggaac tcttctcgga ctggctgatg      1440
accggtcaca tggatcaatt catgtgcttt gtccctacca atgataaaaa caacgaccag      1500
aaggacttcc gcctgctgct ggccagcccc agtgcctgct ttgagctgtt cgaacagaag      1560
cagaaggaag ctatgggaa cgtgaccctg tttgaagaca ttggagcaga acagctcctt      1620
tctaatggga gggagagcaa aactatttcc caaatcctgg ctgacaagag ttttcgagag      1680
cagaacacct atgttgagaa gtgtatcagc ctgaaccgca ccctcctgaa gacagaactg      1740
ggattggagg acaaggacat catcctgatc ccgcagctct tctgcctgga gcagctgacg      1800
aatgtcccct ccaaccagca gagcaccaaa ctcttcgcga ggccgtactt ccccgacatg      1860
ctgcagataa tcgtgttggg caagaaccctt ggaatcccca gccctttgg gcccaaaatc      1920 aatggcacct gctgcctaga agagaaagtg tgtggattac tggagcccct gggtctcaag      1980
tgcaccttca ttgatgattt tgactgctac ctggccaaca taggggacgt ctgtgccagt      2040
gccatcataa acagggtgcc atttgcattc aagtggtgga agatgacccc ataaaccct      2100 ggccctggca cggccagtcc gcgccagtac ggatggcctt tgccatagat agtagtgggt      2160
gcgagcgttg ttgttgcact gggtcgaagg gacggaagct gggagttagg gtctctcaca     2220
tctaccagct tgacacttct ggaggggaaa agggaaaaga gcgccctatgt aaacaaattg     2280 ccatagagcc aataaagcat ggtattctga atacaaaaaa aaaaaaaaaa aaaaaaaaa      2340 a                                                                      2341

<210> SEQ ID NO 2
<211> LENGTH: 664
<212> TYPE: PRT
<213> ORGANISM: Mus musculus

<400> SEQUENCE: 2

Met Val Gly Met Glu Ile Thr Leu Asp Ile Ser Lys Cys Ala Pro Asp
1               5                   10                  15

Lys Cys Lys Ser Phe Thr Ile Arg Gly Ser Pro Arg Ile Leu Ile His
            20                  25                  30

Ile Ser Ser Val Ile Ala Gly Lys Glu Asp Thr Val Val Trp Arg
        35                  40                  45

Ser Met Asn His Pro Thr Val Ala Leu Val Arg Met Val Ala Pro Ser
    50                  55                  60

Pro Thr Val Asp Glu Asp Lys Val Leu Val Ser Tyr Phe Cys Pro Asp
65                  70                  75                  80

Gln Glu Val Pro Thr Ala Thr Ala Val Leu Phe Leu Thr Gly Ile Glu
                85                  90                  95

Ile Ser Leu Glu Ala Asp Ile Tyr Arg Asp Gly Gln Leu Asp Met Pro
            100                 105                 110

Ser Asp Lys Gln Ala Lys Lys Lys Trp Met Trp Gly Met Asn Gly Trp
        115                 120                 125

Gly Ala Ile Leu Leu Val Asn Cys Ser Pro Asn Ala Val Gly Gln Pro
```

-continued

```
            130                 135                 140
Asp Glu Gln Ser Phe Gln Glu Gly Pro Arg Glu Ile Gln Asn Asn Leu
145                 150                 155                 160

Ser Gln Met Asn Val Thr Val Glu Gly Pro Thr Ser Ile Leu Gln Asn
                165                 170                 175

Tyr Gln Leu Ile Leu His Thr Ser Glu Glu Ala Lys Lys Thr Arg
                180                 185                 190

Val Tyr Trp Ser Gln Arg Gly Ser Ser Ala Tyr Glu Leu Val Val Gly
                195                 200                 205

Pro Asn Lys Pro Val Tyr Leu Leu Pro Thr Phe Glu Asn Arg Arg Lys
210                 215                 220

Glu Ala Phe Tyr Val Glu Ala Thr Glu Phe Pro Ser Pro Ser Phe Ser
225                 230                 235                 240

Gly Leu Ile Ser Leu Ser Leu Ser Leu Val Glu Lys Ala His Asp Glu
                245                 250                 255

Cys Ile Pro Glu Ile Pro Leu Tyr Lys Asp Thr Val Met Phe Arg Val
                260                 265                 270

Ala Pro Tyr Ile Phe Met Pro Ser Thr Gln Met Pro Leu Glu Val Tyr
                275                 280                 285

Leu Cys Arg Glu Leu Gln Leu Gln Gly Phe Val Asp Ser Val Thr Lys
                290                 295                 300

Leu Ser Glu Lys Ser Lys Val Gln Val Val Lys Val Tyr Glu Asp Pro
305                 310                 315                 320

Asn Arg Gln Ser Lys Trp Leu Gln Asp Glu Met Ala Phe Cys Tyr Thr
                325                 330                 335

Gln Ala Pro His Lys Thr Val Ser Leu Ile Leu Asp Thr Pro Arg Val
                340                 345                 350

Ser Lys Leu Glu Asp Phe Pro Met Lys Tyr Thr Leu Thr Pro Gly Ser
                355                 360                 365

Gly Tyr Leu Ile Arg Gln Ile Glu Asp His Arg Val Ala Ser Leu Asp
                370                 375                 380

Ser Ile Gly Asn Leu Met Val Ser Pro Val Lys Ala Gln Gly Lys
385                 390                 395                 400

Asp Tyr Pro Leu Gly Arg Val Leu Ile Gly Gly Ser Phe Tyr Pro Ser
                405                 410                 415

Ser Glu Gly Arg Asp Met Asn Lys Gly Leu Arg Glu Phe Val Tyr Ala
                420                 425                 430

Gln Gln Val Gln Ala Pro Val Glu Leu Phe Ser Asp Trp Leu Met Thr
                435                 440                 445

Gly His Met Asp Gln Phe Met Cys Phe Val Pro Thr Asn Asp Lys Asn
450                 455                 460

Asn Asp Gln Lys Asp Phe Arg Leu Leu Leu Ala Ser Pro Ser Ala Cys
465                 470                 475                 480

Phe Glu Leu Phe Glu Gln Lys Gln Lys Glu Gly Tyr Gly Asn Val Thr
                485                 490                 495

Leu Phe Glu Asp Ile Gly Ala Glu Gln Leu Leu Ser Asn Gly Arg Glu
                500                 505                 510

Ser Lys Thr Ile Ser Gln Ile Leu Ala Asp Lys Ser Phe Arg Glu Gln
                515                 520                 525

Asn Thr Tyr Val Glu Lys Cys Ile Ser Leu Asn Arg Thr Leu Leu Lys
                530                 535                 540

Thr Glu Leu Gly Leu Glu Asp Lys Asp Ile Ile Leu Ile Pro Gln Leu
545                 550                 555                 560
```

```
Phe Cys Leu Glu Gln Leu Thr Asn Val Pro Ser Asn Gln Ser Thr
            565                 570                 575

Lys Leu Phe Ala Arg Pro Tyr Phe Pro Asp Met Leu Gln Ile Ile Val
            580                 585                 590

Leu Gly Lys Asn Leu Gly Ile Pro Lys Pro Phe Gly Pro Lys Ile Asn
            595                 600                 605

Gly Thr Cys Cys Leu Glu Glu Lys Val Cys Gly Leu Leu Glu Pro Leu
            610                 615                 620

Gly Leu Lys Cys Thr Phe Ile Asp Asp Phe Asp Cys Tyr Leu Ala Asn
625                 630                 635                 640

Ile Gly Asp Val Cys Ala Ser Ala Ile Ile Asn Arg Val Pro Phe Ala
                    645                 650                 655

Phe Lys Trp Trp Lys Met Thr Pro
            660

<210> SEQ ID NO 3
<211> LENGTH: 2701
<212> TYPE: DNA
<213> ORGANISM: Mus musculus
<220> FEATURE:
<221> NAME/KEY: misc_feature
<222> LOCATION: (2337)..(2337)
<223> OTHER INFORMATION: "n" meaning any nucleotide selected from A, T,
      G or C
<220> FEATURE:
<221> NAME/KEY: misc_feature
<222> LOCATION: (2340)..(2340)
<223> OTHER INFORMATION: "n" meaning any nucleotide selected from A, T,
      G or C
<220> FEATURE:
<221> NAME/KEY: misc_feature
<222> LOCATION: (2366)..(2366)
<223> OTHER INFORMATION: "n" meaning any nucleotide selected from A, T,
      G or C
<220> FEATURE:
<221> NAME/KEY: misc_feature
<222> LOCATION: (2382)..(2382)
<223> OTHER INFORMATION: "n" meaning any nucleotide selected from A, T,
      G or C
<220> FEATURE:
<221> NAME/KEY: misc_feature
<222> LOCATION: (2447)..(2447)
<223> OTHER INFORMATION: "n" meaning any nucleotide selected from A, T,
      G or C
<220> FEATURE:
<221> NAME/KEY: misc_feature
<222> LOCATION: (2453)..(2453)
<223> OTHER INFORMATION: "n" meaning any nucleotide selected from A, T,
      G or C
<220> FEATURE:
<221> NAME/KEY: misc_feature
<222> LOCATION: (2481)..(2481)
<223> OTHER INFORMATION: "n" meaning any nucleotide selected from A, T,
      G or C
<220> FEATURE:
<221> NAME/KEY: misc_feature
<222> LOCATION: (2509)..(2509)
<223> OTHER INFORMATION: "n" meaning any nucleotide selected from A, T,
      G or C
<220> FEATURE:
<221> NAME/KEY: misc_feature
<222> LOCATION: (2525)..(2525)
<223> OTHER INFORMATION: "n" meaning any nucleotide selected from A, T,
      G or C
<220> FEATURE:
<221> NAME/KEY: misc_feature
<222> LOCATION: (2556)..(2556)
<223> OTHER INFORMATION: "n" meaning any nucleotide selected from A, T,
      G or C
<220> FEATURE:
<221> NAME/KEY: misc_feature
```

```
<222> LOCATION: (2577)..(2577)
<223> OTHER INFORMATION: "n" meaning any nucleotide selected from A, T,
      G or C
<220> FEATURE:
<221> NAME/KEY: misc_feature
<222> LOCATION: (2580)..(2580)
<223> OTHER INFORMATION: "n" meaning any nucleotide selected from A, T,
      G or C
<220> FEATURE:
<221> NAME/KEY: misc_feature
<222> LOCATION: (2630)..(2630)
<223> OTHER INFORMATION: "n" meaning any nucleotide selected from A, T,
      G or C
<220> FEATURE:
<221> NAME/KEY: misc_feature
<222> LOCATION: (2666)..(2666)
<223> OTHER INFORMATION: "n" meaning any nucleotide selected from A, T,
      G or C

<400> SEQUENCE: 3
gactcactat agggctcgag cggccgcccg ggcaggtatg gcttctgcgt tgctcctgct      60
ccctgacatg cttgagttcc agtcctgacg tccttggtga taaacagcag catggaacta     120
agctctgggg tctgccctgc cactagactc caggaagcag aaaaggcagc tgtgcacaaa     180
cgcagtccca aggttttgga ggctctacga aagctcaaca tccaagctga ccaggctcca     240
gtcattgctg tcttgggctc tggcgggggg ctgcgggccc acatcgcttg tcttggtgtg     300
ctgagtgagc tgaaagaact tggcctgttg gatgctgtca catacctcgc agggtctct      360
gggtccactt gggcactgtc ttcactctac accaagaatg aaatatgga agggatagaa      420
gaggagctga acatcggta tgagaagaat gagtgggact tcatgagag cctggagaaa      480
gccatccagg catcaaagag ggagaattac tccctgactg acttttgggc ctatttaatt     540
gtttccaggc aaatcagaga acttcaggat tcgaatttgt ccagtctaaa gaagcaagtg     600
gaagaaggag tgctgcccta tcccatcttt gcagccattg atgaggacct tctggctgat     660
tggagggaga ggaaaactca gaattcctgg tttgaattca ctcctcatca tgctggctac     720
cctgcacttg ggcttatgt ccccatcaca gagtttggaa gcagatttga aatgggaaa      780
ctggttaaat ctgagcctga gagagattg acttcctga gaggtttatg gggaagtgct      840
tttgctgata ttaaagaaat taagaattat attttgaact acttcaggaa ccccttggaa    900
aaattgaagt ttatagaagg accagtgaca tactcagaag caccaggat gaatgtggat     960
gcaatgctct tggatttagt gatggcttat ttcacagata tgaatgaccc cagcatcaag   1020
gataagctct gtgcccttca gcaggctctg gtactgaga cagatgaatt tggcatagag   1080
atggctgaga tcatccagaa ttggaatgag acctccgcag agaagaagga gcagtttctc   1140
gaccatctgt tggatcgctt caagaagaca caagaagaca ccaccacata cagtttgatg   1200
aactggaaca cgggtctagt ttgggaccgt tgcgttttg tgaatgaaac tcgcaagtgt   1260
gtctccaaat ggcagtgggg aactgtttac aacttcctct ataaacacgg taaaattgca   1320
gatgagacca tgtgcagccg agagcttctc catctggtgg atgctggttt tgccatcaac   1380
actccctatc cacttgttct gcctcctgtg cgtgaaactc acctcatcct ctcatttgac   1440
ttcagtgctg gggacccact agagaccatc agggccacag cagactactg ccaacgccat   1500
gaaatcccct ttcctgaggt gagcgaggat cagttgaagg aatgggccaa agccccagca   1560
agctgctatg tcctcagagg ggaaacagga cctgttgtca tgcactttac tctgttcaac   1620
aaagacaact gtgagatga tattgagaca tggagaaaaa aatatgggac agtaaaacta   1680
tctgactcat acacaccaga cctggtgaga gatttgctga gggtatccaa ggagaatgtg   1740
```

-continued

```
aagaaaaaca aaattaatat cctcagtgag atgaggaaag tggctgggaa tcctgggaac   1800
atcccaagag tgaacaagga ggcctgcttg ggagacagag taaggatcc ccaaggctct    1860
cagactgtgg agtttaagaa atcccacaac atatctaagg attaaggatc ctttgcacta   1920
cctggagagt tggcatctat tagtggactc accacctgtg ctctctccaa agtccaccgt   1980
aagctgtctc tttgtgaaga agaactgcag ttttcagggt actgtgggcc tactgcttta   2040
ccagggccca agtgtcaacc tggcctgatg ttctctgcca ctcataaaat tgcatttgcc   2100
ttagctatta ccattgagca agtctccaga gacctagatg gtgtctttga tagcattatt   2160
tagggcactg ggtcaccaga gctaaaagag gcaaagtatg ttcttcagat acctcagggg   2220
accctaaagc tagagcacaa ctccttgatc atcaaagcca ccctgtccaa catccatgtg   2280
gttaaaatga atgtagtgat tgagaccaaa gcctcataaa ttttctctc attcttnatn    2340
tgctcatttt atacacccag tcttantaat tttttttttt tntataaaag gatagacctt   2400
agctcaaatc atgacccatc acttcagagc aattaaaaaa acccagncaa ctntgagaag   2460
acatgttctg tatatgcttg ngtatctgct gccttagtgc ctccttccng cttgcctact   2520
tcctntcctt tccatcccctt ccacctgtaa cttttnttg atttggattc cacaatnttn   2580
tcattgtaat atcacaggca agttccttca catgaattcc tttaatcatn tatggaataa   2640
atgtgcattg tggttgtgcc ctggtntttc caaaaaaaaa aaaaaaaaaa aaaaaaaaa    2700
a                                                                  2701
```

<210> SEQ ID NO 4
<211> LENGTH: 597
<212> TYPE: PRT
<213> ORGANISM: Mus musculus

<400> SEQUENCE: 4

```
Met Glu Leu Ser Ser Gly Val Cys Pro Ala Thr Arg Leu Gln Glu Ala
1               5                   10                  15
Glu Lys Ala Ala Val His Lys Arg Ser Pro Lys Val Leu Glu Ala Leu
                20                  25                  30
Arg Lys Leu Asn Ile Gln Ala Asp Gln Ala Pro Val Ile Ala Val Leu
            35                  40                  45
Gly Ser Gly Gly Gly Leu Arg Ala His Ile Ala Cys Leu Gly Val Leu
        50                  55                  60
Ser Glu Leu Lys Glu Leu Gly Leu Leu Asp Ala Val Thr Tyr Leu Ala
65                  70                  75                  80
Gly Val Ser Gly Ser Thr Trp Ala Leu Ser Ser Leu Tyr Thr Lys Asn
                85                  90                  95
Gly Asn Met Glu Gly Ile Glu Glu Leu Lys His Arg Tyr Glu Lys
                100                 105                 110
Asn Glu Trp Asp Phe His Glu Ser Leu Glu Lys Ala Ile Gln Ala Ser
            115                 120                 125
Lys Arg Glu Asn Tyr Ser Leu Thr Asp Phe Trp Ala Tyr Leu Ile Val
        130                 135                 140
Ser Arg Gln Ile Arg Glu Leu Gln Asp Ser Asn Leu Ser Ser Leu Lys
145                 150                 155                 160
Lys Gln Val Glu Glu Gly Val Leu Pro Tyr Pro Ile Phe Ala Ala Ile
                165                 170                 175
Asp Glu Asp Leu Leu Ala Asp Trp Arg Glu Arg Lys Thr Gln Asn Ser
            180                 185                 190
Trp Phe Glu Phe Thr Pro His His Ala Gly Tyr Pro Ala Leu Gly Ala
```

```
                195                 200                 205
Tyr Val Pro Ile Thr Glu Phe Gly Ser Arg Phe Glu Asn Gly Lys Leu
210                 215                 220

Val Lys Ser Glu Pro Glu Arg Asp Leu Thr Phe Leu Arg Gly Leu Trp
225                 230                 235                 240

Gly Ser Ala Phe Ala Asp Ile Lys Glu Ile Lys Asn Tyr Ile Leu Asn
                245                 250                 255

Tyr Phe Arg Asn Pro Phe Gly Lys Leu Lys Phe Ile Glu Gly Pro Val
                260                 265                 270

Thr Tyr Ser Glu Ala Pro Arg Met Asn Val Asp Ala Met Leu Leu Asp
                275                 280                 285

Leu Val Met Ala Tyr Phe Thr Asp Met Asn Asp Pro Ser Ile Lys Asp
290                 295                 300

Lys Leu Cys Ala Leu Gln Gln Ala Leu Gly Thr Glu Thr Asp Glu Phe
305                 310                 315                 320

Gly Ile Glu Met Ala Glu Ile Ile Gln Asn Trp Asn Glu Thr Ser Ala
                325                 330                 335

Glu Lys Lys Glu Gln Phe Leu Asp His Leu Leu Asp Arg Phe Lys Lys
                340                 345                 350

Thr Gln Glu Asp Thr Thr Thr Tyr Ser Leu Met Asn Trp Asn Thr Gly
                355                 360                 365

Leu Val Trp Asp Arg Cys Val Phe Val Asn Glu Thr Arg Lys Cys Val
370                 375                 380

Ser Lys Trp Gln Trp Gly Thr Val Tyr Asn Phe Leu Tyr Lys His Gly
385                 390                 395                 400

Lys Ile Ala Asp Glu Thr Met Cys Ser Arg Glu Leu Leu His Leu Val
                405                 410                 415

Asp Ala Gly Phe Ala Ile Asn Thr Pro Tyr Pro Leu Val Leu Pro Pro
                420                 425                 430

Val Arg Glu Thr His Leu Ile Leu Ser Phe Asp Phe Ser Ala Gly Asp
                435                 440                 445

Pro Leu Glu Thr Ile Arg Ala Thr Ala Asp Tyr Cys Gln Arg His Glu
                450                 455                 460

Ile Pro Phe Pro Glu Val Ser Glu Asp Gln Leu Lys Glu Trp Ala Lys
465                 470                 475                 480

Ala Pro Ala Ser Cys Tyr Val Leu Arg Gly Glu Thr Gly Pro Val Val
                485                 490                 495

Met His Phe Thr Leu Phe Asn Lys Asp Asn Cys Gly Asp Asp Ile Glu
                500                 505                 510

Thr Trp Arg Lys Lys Tyr Gly Thr Val Lys Leu Ser Asp Ser Tyr Thr
                515                 520                 525

Pro Asp Leu Val Arg Asp Leu Leu Arg Val Ser Lys Glu Asn Val Lys
530                 535                 540

Lys Asn Lys Ile Asn Ile Leu Ser Glu Met Arg Lys Val Ala Gly Asn
545                 550                 555                 560

Pro Gly Asn Ile Pro Arg Val Asn Lys Glu Ala Cys Leu Gly Asp Arg
                565                 570                 575

Val Lys Asp Pro Gln Gly Ser Gln Thr Val Glu Phe Lys Lys Ser His
                580                 585                 590

Asn Ile Ser Lys Asp
                595

<210> SEQ ID NO 5
```

```
<211> LENGTH: 11
<212> TYPE: PRT
<213> ORGANISM: Mus musculus

<400> SEQUENCE: 5

Gln Asp Trp Asp Phe His Glu Ser Asn Gln Lys
1               5                   10

<210> SEQ ID NO 6
<211> LENGTH: 6
<212> TYPE: PRT
<213> ORGANISM: Mus musculus
<220> FEATURE:
<221> NAME/KEY: MISC_FEATURE
<222> LOCATION: (4)..(4)
<223> OTHER INFORMATION: "Xaa" meaning any amino acid
<220> FEATURE:
<221> NAME/KEY: MISC_FEATURE
<222> LOCATION: (5)..(5)
<223> OTHER INFORMATION: "Xaa" meaning any amino acid

<400> SEQUENCE: 6

Val Cys Gly Xaa Xaa Glu
1               5

<210> SEQ ID NO 7
<211> LENGTH: 2341
<212> TYPE: DNA
<213> ORGANISM: Mus musculus

<400> SEQUENCE: 7
gggtaaggac tgctgacagt ggctagcttg gtaagcccag ccatgtcttt tcagaactca      60
ctcagcctgt ctctggtcaa tcccacccat gccctctgca tggtaggcat ggaaatcacc     120
ttggacatca gcaagtgtgc accggacaag tgcaagtctt tcaccatccg tggttccccc     180
aggatcttga tccacatctc tagctccgtc atcgctggca agaggacac tgtggtctgg      240 aggtcaatga accatcccac agtggcattg gtgaggatgg tggcgcccag ccccactgtg     300
gatgaagaca aggtgctggt ctcctacttc tgtcctgacc aagaagtccc cacggccaca     360
gctgtgctgt ttctcaccgg catcgagatc tccctggagg cagacatcta tcgagatgga     420
caactggaca tgccaagtga taagcaagct aagaaaaaat ggatgtgggg tatgaacggc     480
tggggagcca tcctgcttgt gaattgtagc cctaatgctg tgggccagcc tgatgaacag     540
tcctttcagg agggcccag agaaatacag aacaacctgt ctcagatgaa tgtaactgtg      600
gagggcccca ccagcatcct acagaattac cagttgatcc tacatacctc cgaagaagag     660
gcgaagaaga caagagtcta ctggtctcag agaggctcct ctgcgtatga actggtggtg     720
ggacccaaca agcctgtcta tctcctgcct acctttgaga accgtaggaa agaggctttc     780
tacgtagaag ccacggaatt cccatctccc agcttctcgg gcctgatctc cttgtcactc     840
tccctagtag aaaaggctca cgacgagtgc atcccagaga ttccgctcta aggataca      900 gtgatgttcc gggtggcacc ttatatcttc atgcccagca cccagatgcc tctagaggtt     960
tacctgtgca gggagctaca gctgcaaggc tttgtggact cagtgaccaa gctgagcgag    1020
aagagcaaag tgcaggtggt aaaggtctat gaggacccca accgccagag caagtggctc    1080
caggacgaga tggctttctg ctatactcag gctcctcaca gacggtgtc attgatcctt     1140 gacacccaa gggtttccaa gctggaagac ttccccatga atacacact gaccctggc       1200 tctggctacc tgatccgaca aattgaggac caccgggtgg ctagcctgga ttccatcggg    1260
aacctgatgg tatctccgcc tgtcaaggct cagggcaaag actaccctct agggagggtc    1320
```

-continued

```
ctcattggtg gcagctttta ccccagctct gagggccggg acatgaacaa gggcctgcga    1380
gaattcgtgt atgcccagca ggtgcaggcc cctgtggaac tcttctcgga ctggctgatg    1440
accggtcaca tggatcaatt catgtgcttt gtccctacca atgataaaaa caacgaccag    1500
aaggacttcc gcctgctgct ggccagcccc agtgcctgct ttgagctgtt cgaacagaag    1560
cagaaggaag gctatgggaa cgtgaccctg tttgaagaca ttggagcaga acagctcctt    1620
tctaatggga gggagagcaa aactatttcc caaatcctgg ctgacaagag ttttcgagag    1680
cagaacacct atgttgagaa gtgtatcagc ctgaaccgca ccctcctgaa gacagaactg    1740
ggattggagg acaaggacat catcctgatc ccgcagctct tctgcctgga gcagctgacg    1800
aatgtcccct ccaaccagca gagcaccaaa ctcttcgcga ggccgtactt ccccgacatg    1860
ctgcagataa tcgtgttggg caagaacctt ggaatcccca agccctttgg gcccaaaatc    1920
aatggcacct gctgcctaga agagaaagtg tgtggattac tggagcccct gggtctcaag    1980
tgcaccttca ttgatgattt tgactgctac ctggccaaca tagggacgt ctgtgccagt    2040
gccatcataa acagggtgcc atttgcattc aagtggtgga agatgacccc ataaacccct    2100
ggccctggca cggccagtcc gcgccagtac ggatggcctt tgccatagat agtagtgggt    2160
gcgagcgttg ttgttgcact gggtcgaagg gacggaagct gggagttagg gtctctcaca    2220
tctaccagct tgacacttct ggaggggaaa agggaaaaga gcgcctatgt aaacaaattg    2280
ccatagagcc aataaagcat ggtattctga atacaaaaaa aaaaaaaaaa aaaaaaaaa    2340
a                                                                   2341
```